(12) United States Patent
Hamilton et al.

(10) Patent No.: US 8,846,613 B2
(45) Date of Patent: Sep. 30, 2014

(54) PHARMACEUTICAL COMBINATIONS FOR THE TREATMENT OF METABOLIC DISORDERS

(71) Applicants: Bradford S. Hamilton, Biberach an der Riss (DE); Thomas Rauch, Ehingen-Risstissen (DE); Manami Tsutsumi, Stratford, CT (US)

(72) Inventors: Bradford S. Hamilton, Biberach an der Riss (DE); Thomas Rauch, Ehingen-Risstissen (DE); Manami Tsutsumi, Stratford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/048,880

(22) Filed: Oct. 8, 2013

(65) Prior Publication Data

US 2014/0038888 A1   Feb. 6, 2014

Related U.S. Application Data

(63) Continuation of application No. 13/855,835, filed on Apr. 3, 2013, now abandoned, which is a continuation of application No. 13/285,047, filed on Oct. 31, 2011, now abandoned.

(60) Provisional application No. 61/409,241, filed on Nov. 2, 2010.

(51) Int. Cl.
| | |
|---|---|
| *A61K 31/5355* | (2006.01) |
| *A61K 45/06* | (2006.01) |
| *A61K 31/7048* | (2006.01) |
| *A61K 31/522* | (2006.01) |
| *A61K 31/155* | (2006.01) |
| *A61K 31/422* | (2006.01) |
| *A61K 31/427* | (2006.01) |

(52) U.S. Cl.
CPC ............ *A61K 31/5355* (2013.01); *A61K 45/06* (2013.01); *A61K 31/7048* (2013.01); *A61K 31/522* (2013.01); *A61K 31/155* (2013.01); *A61K 31/422* (2013.01); *A61K 31/427* (2013.01)
USPC ............ 514/6.3; 514/228.8; 514/6.5; 514/61; 514/23; 514/6.9; 514/7.2

(58) Field of Classification Search
None
See application file for complete search history.

(56) References Cited

U.S. PATENT DOCUMENTS

| | | |
|---|---|---|
| 3,341,538 A | 9/1967 | Block et al. |
| 3,378,587 A | 4/1968 | Reinhardt |
| 3,681,349 A | 8/1972 | Schwan et al. |
| 3,703,529 A | 11/1972 | Cavalla et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 4,268,673 A | 5/1981 | Akkerman et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |

(Continued)

FOREIGN PATENT DOCUMENTS

| | | |
|---|---|---|
| DE | 1801556 A1 | 5/1970 |
| DE | 19918725 A1 | 10/2000 |

(Continued)

OTHER PUBLICATIONS

Abstract in English for DE10034623, Publication Date Jan. 31, 2002.

(Continued)

*Primary Examiner* — Karlheinz R Skowronek
*Assistant Examiner* — Schuyler Milton
(74) *Attorney, Agent, or Firm* — Michael P. Morris; David L. Kershner

(57) ABSTRACT

The invention relates to a pharmaceutical composition comprising 1.a and/or 1.b according to claim 1 in combination with at least one second therapeutic agent 2 which is suitable in the treatment or prevention of one or more conditions selected from type 1 diabetes mellitus, type 2 diabetes mellitus, impaired glucose tolerance and hyperglycemia. In addition the present invention relates to methods for preventing or treating of metabolic disorders and related conditions.

17 Claims, No Drawings

(56) References Cited

U.S. PATENT DOCUMENTS

| | | |
|---|---|---|
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1* | 5/2012 | Renz et al. .......... 514/228.8 |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| DE | 19929348 A1 | 12/2000 |
| DE | 10034623 A1 | 1/2002 |
| EP | 0415642 A1 | 3/1991 |
| EP | 0454444 A1 | 10/1991 |
| EP | 0471591 A2 | 2/1992 |
| EP | 0640594 A1 | 3/1995 |
| EP | 0645387 A1 | 3/1995 |
| EP | 0928789 A1 | 7/1999 |
| EP | 1156049 A1 | 11/2001 |
| EP | 1270724 A2 | 1/2003 |
| EP | 1801098 A1 | 6/2007 |
| EP | 1852425 A1 | 11/2007 |
| EP | 1864971 A1 | 12/2007 |
| EP | 1935420 A1 | 6/2008 |
| GB | 1077711 A | 8/1967 |
| JP | 6092945 | 4/1994 |
| JP | 7157681 | 6/1995 |
| JP | 09151179 | 6/1997 |
| JP | 2002179572 A | 6/2002 |
| JP | 2003096058 A | 4/2003 |
| JP | 2003300884 A | 10/2003 |
| JP | 2005206503 A | 8/2005 |
| JP | 2005239670 A | 9/2005 |
| JP | 2005272321 A | 10/2005 |
| JP | 2007140188 A | 6/2007 |
| JP | 2007254409 A | 10/2007 |
| JP | 2009110842 A | 5/2009 |
| JP | 2011519374 A | 7/2011 |
| WO | 9207838 A1 | 5/1992 |
| WO | 9307128 A1 | 4/1993 |
| WO | 9313103 A1 | 7/1993 |
| WO | 9531440 A1 | 11/1995 |
| WO | 9614297 A1 | 5/1996 |
| WO | 9623787 A1 | 8/1996 |
| WO | 9637494 A1 | 11/1996 |
| WO | 9707789 A1 | 3/1997 |
| WO | 9736605 A1 | 10/1997 |
| WO | 9822462 A1 | 5/1998 |
| WO | 9857940 A1 | 12/1998 |
| WO | 9905125 A1 | 2/1999 |
| WO | 9906395 A1 | 2/1999 |
| WO | 0009107 A2 | 2/2000 |
| WO | 0100595 A1 | 1/2001 |
| WO | 0113917 A1 | 3/2001 |

(56) References Cited

FOREIGN PATENT DOCUMENTS

| | | |
|---|---|---|
| WO | 0144200 A2 | 6/2001 |
| WO | 0155063 A1 | 8/2001 |
| WO | 0206244 A1 | 1/2002 |
| WO | 0206277 A1 | 1/2002 |
| WO | 0222572 A2 | 3/2002 |
| WO | 03043988 A1 | 5/2003 |
| WO | 03057673 A1 | 7/2003 |
| WO | 03093261 A1 | 11/2003 |
| WO | 03097608 A2 | 11/2003 |
| WO | 2004004722 A1 | 1/2004 |
| WO | 2004009559 A2 | 1/2004 |
| WO | 2004014859 A2 | 2/2004 |
| WO | 2004046137 A1 | 6/2004 |
| WO | 2004056745 A2 | 7/2004 |
| WO | 2004089896 A1 | 10/2004 |
| WO | 2004094375 A2 | 11/2004 |
| WO | 2005000845 A1 | 1/2005 |
| WO | 2005086700 A2 | 9/2005 |
| WO | 2005108360 A1 | 11/2005 |
| WO | 2005108361 A1 | 11/2005 |
| WO | 2005113525 A1 | 12/2005 |
| WO | 2005116002 A2 | 12/2005 |
| WO | 2006002349 A1 | 1/2006 |
| WO | 2006003494 A2 | 1/2006 |
| WO | 2006014357 A1 | 2/2006 |
| WO | 2006017443 A2 | 2/2006 |
| WO | 2006024627 A2 | 3/2006 |
| WO | 2006024628 A1 | 3/2006 |
| WO | 2006031715 A2 | 3/2006 |
| WO | 2006040329 A1 | 4/2006 |
| WO | 2006044174 A2 | 4/2006 |
| WO | 2006049952 A1 | 5/2006 |
| WO | 2006066924 A2 | 6/2006 |
| WO | 2006066948 A1 | 6/2006 |
| WO | 2006090792 A1 | 8/2006 |
| WO | 2006104280 A1 | 10/2006 |
| WO | 2006109056 A1 | 10/2006 |
| WO | 2007008529 A2 | 1/2007 |
| WO | 2007022371 A2 | 2/2007 |
| WO | 2007048595 A1 | 5/2007 |
| WO | 2007051810 A2 | 5/2007 |
| WO | 2007061661 A2 | 5/2007 |
| WO | 2007068330 A1 | 6/2007 |
| WO | 2007076055 A2 | 7/2007 |
| WO | 2007079186 A1 | 7/2007 |
| WO | 2007081569 A2 | 7/2007 |
| WO | 2007081570 A2 | 7/2007 |
| WO | 2007081571 A2 | 7/2007 |
| WO | 2007084314 A2 | 7/2007 |
| WO | 2007101270 A1 | 9/2007 |
| WO | 2007103719 A2 | 9/2007 |
| WO | 2007109456 A2 | 9/2007 |
| WO | 2007118185 A2 | 10/2007 |
| WO | 2007123853 A2 | 11/2007 |
| WO | 2007124254 A2 | 11/2007 |
| WO | 2007124329 A1 | 11/2007 |
| WO | 2007124337 A1 | 11/2007 |
| WO | 2007127693 A1 | 11/2007 |
| WO | 2007127763 A2 | 11/2007 |
| WO | 2008000951 A2 | 1/2008 |
| WO | 2008024497 A2 | 2/2008 |
| WO | 2008031227 A1 | 3/2008 |
| WO | 2008036715 A1 | 3/2008 |
| WO | 2008046578 A2 | 4/2008 |
| WO | 2008046758 A2 | 4/2008 |
| WO | 2008059948 A1 | 5/2008 |
| WO | 2008106128 A2 | 9/2008 |
| WO | 2008118332 A2 | 10/2008 |
| WO | 2009017671 A1 | 2/2009 |
| WO | 2009020140 A1 | 2/2009 |
| WO | WO 2009017664 A1 * | 2/2009 |
| WO | 2009061498 A1 | 5/2009 |
| WO | 2009063061 A2 | 5/2009 |
| WO | 2009075835 A1 | 6/2009 |
| WO | 2009088997 A1 | 7/2009 |
| WO | 2009094169 A1 | 7/2009 |
| WO | 2009100872 A1 | 8/2009 |
| WO | 2009102428 A2 | 8/2009 |
| WO | 2009102460 A2 | 8/2009 |
| WO | 2009107664 A1 | 9/2009 |
| WO | 2009108332 A1 | 9/2009 |
| WO | 2009117109 A1 | 9/2009 |
| WO | 2009131669 A2 | 10/2009 |
| WO | 2009134384 A1 | 11/2009 |
| WO | 2009134387 A1 | 11/2009 |
| WO | 2009134392 A1 | 11/2009 |
| WO | 2009134400 A1 | 11/2009 |
| WO | 2009138386 A2 | 11/2009 |
| WO | 2010010149 A1 | 1/2010 |
| WO | 2010010150 A1 | 1/2010 |
| WO | 2010010157 A2 | 1/2010 |
| WO | 2010010174 A1 | 1/2010 |
| WO | 2010011314 A1 | 1/2010 |
| WO | 2010023161 A1 | 3/2010 |
| WO | 2010046445 A2 | 4/2010 |
| WO | 2010089303 A1 | 8/2010 |
| WO | 2010091067 A2 | 8/2010 |
| WO | 2010104830 A1 | 9/2010 |
| WO | 2010127237 A2 | 11/2010 |
| WO | 2010139673 A1 | 12/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011056737 A1 | 5/2011 |
| WO | 2011057054 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

Aluri, B.R. et al., "Bulky n-Substituted 1,3-Benzazaphospholes: Access via Pd-Catalyzed C-N and C-P Cross Coupling, Lithiation, and Conversion to Novel P=C PtBu2 Hybrid Ligands". Inorganic Chemistry, 2008, 47, p. 6900-6912.

Aluri, B.R. et al., "Sterically and Polarity-Controlled Reactions of tBuLi with P=CH-NR Heterocycles: Novel Heterocyclic P- and P,O-Ligands and Preliminary Tests in Transition-Metal Catalysis", Chem. Eur. Journal, vol. 14, 2008, p. 4328-4335.

ChemAbstract—Accession #: 1969:68280. Maillard, J. et al., "Spiroheterocyclic cycloalkane compounds II. Synthesis of 6-substituted-tetrahydro-2H-1, 3-oxazine-2-ones." Chima Therapeutica, 3(5), 1968, pp. 321-324.

ChemAbstract—Accession #: 1978:563520. Slyusarenko, E.I., et al., Syntheses based on thionylamides. IV. 2-alkoxy-5,6-dihydro-1,3-oxazines. Zhurnal Organicheskoi Chimii, 14(5), 1979, p. 1093.

ChemAbstract—Accession #: 1983:595067. Saitkulova, F.G. et al., "Syntheses involving bromozinc alcholates of carboxylic acid esters". Khimiya Elementoorganicheskikh Soedinii, vol. 1982, 1982, pp. 22-26.

ChemAbstract—Accession #: 1983:89280. Lapkin, I.I. et al., "Synthesis of 1,3-oxazine-2,4-diones." Zhurnal Organicheskoi Khimii, vol. 18, No. 11, 1982, p. 2468.

ChemAbstract—Accession No. 2007:1110441 Abstract, Chemical Abstract Service, Columbus, Ohio, Fukushima, H. et al., "Preparation of imidazolidinone derivatives as 11.beta.-HSD1 inhibitors". JP2007254409 (Taisho Pharmaceutical Co. Ltd., Japan, Oct. 4, 2007. (Attached is a machine translation of the ChemAbstract and a Derwent World Patents Index file record).

ChemAbstract: CAS: 150:214405, Accession #: 2009:140024. Claremon, D.A., et al., Preparation of 1,3-oxazinan-2-one dervatives as inhibitors of 11-beta-hydroxysteroid dehydrogenase type1. 2009.

Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.

Evans, B.E. et al., "Orally active, nonpeptide osytocin antagonists". Journal of Medicinal Chemistry, American Chem. Soc., Vo. 35, No. 21, Oct. 15, 1992, p. 3919-3927.

(56) References Cited

OTHER PUBLICATIONS

Fandrick, D.R. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.

Goubet, F. et al., "Conversion of a Thiohydantoin to the Corresponding Hydantoin via a Ring-Opening/Ring Closure Mechanism". Tetrahedron Letters, Elsevier, Amsterdam, vol. 37. No. 43, Oct. 21, 1996. p. 7727-7730.

Harno, E. et al., "Will treating diabetes with 11-beta-HSD1 inhibitors affect the HPA axis?" Trends in Endocrinology and Metabolism, Elsevier Science Publishing, NY, NY, USm, vol. 21, No. 10, Oct. 1, 2010, pp. 619-627.

International Search Report for PCT/EP2011/068938 mailed Mar. 27, 2012.

Kashima, C. et al., "Preparation of N-Aryl-2,4-diaminopentanes by the Ring Opening Reaction of 1-Aryl-3,4,5,6-tetradydro-2-(1H)pyrimidinones". Journal of Heterocyclic Chemistry, vol. 18, 1981, p. 1595-1596.

Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.

Muehlstadt, M. et al., "Cyclisation reactions of beta,gamma-unsaturated derivatives of carbonis acid. IX" Journal Fuer Praktische Chemi, vol. 328, 1986, p. 163-172.

Rosenstock, J. et al., "The 11-beta-hydroxysteroid Dehydrogenase Type 1 inhibitor INCB13739 Improves Hyperglycemia in Patients with Type 2 Diabetes Inadequately Controlled by Metformin Monotherapy." Diabetes Care, vol. 33, No. 7, Jul. 2010, pp. 1516-1522.

Schoellkopf, U. et al., "Umsetzungen Alphametallierter Isocyanide Mit Eigigen 1,3-Dipolen" English: "Reactions of alpha-metalated osicyanidews with some 1,3-dipoles", Liebigs Annalen Der Chemie, Verlag Chemi, GmbH, Weinheim, DE, vol. 4, Jan. 1, 1980, p. 600-610.

Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.

Shibata, I. et al., "Cycloaddition of Oxetanes with Heterocumulenes Catalyzed by Organotin Iodine—Lewis Base Complex". Journal of Heterocyclic Chemistry, vol. 24, 1987, p. 361-363.

Stewart, P. et al., "11beta-hydroxysteroid Dehydrogenase." Vitamins and Hormones—Advances in Research and Applications, 1999, vol. 57, pp. 249-324.

Tadayyon M. et al., "Insulin sensitisation in the treatment of Type 2 diabetes." Expert Opinion on Investigational Drugs, Ashley Publications, Ltd., London, GB, vol. 12, n. 3, Mar. 1, 2003, pp. 307-324.

Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.

Tamaru, Y. et al., "Urea as the Most Reactive and Versatile Nitrogen Nucleophile for the Palladium (2+)-Catalyzed Cyclization of Unsaturated Amines," J. Am. Chem. Soc., 1988, 110, 3994-4002.

Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.

Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.

Worthy, A.D. et al., "Regioselective Hydroformylation of Sulfonamides using a Scaffolding Ligand". Organic Letters, 2009, vol. 11, No. 13—p. 2764-2767.

* cited by examiner

PHARMACEUTICAL COMBINATIONS FOR THE TREATMENT OF METABOLIC DISORDERS

TECHNICAL FIELD OF THE INVENTION

The invention is directed to pharmaceutical combinations comprising an inhibitor of 11-beta-hydroxysteroid dehydrogenase 1 of formula 1.a or 1.b as one active ingredient in combination with at least one additional active ingredient 2 which is suitable in the treatment or prevention of one or more conditions selected from type 1 diabetes mellitus, type 2 diabetes mellitus, impaired glucose tolerance, impaired fasting blood glucose, hyperglycemia, dyslipidemia/hyperlipidemia.

Furthermore the invention relates to methods
for preventing, slowing progression of, delaying, or treating a metabolic disorder;
for improving glycemic control and/or for reducing of fasting plasma glucose, of postprandial plasma glucose and/or of glycosylated hemoglobin HbA1c;
for preventing, slowing, delaying or reversing progression from impaired glucose tolerance, impaired fasting blood glucose, insulin resistance and/or from metabolic syndrome to type 2 diabetes mellitus;
for preventing, slowing progression of, delaying or treating of a condition or disorder selected from the group consisting of complications of diabetes mellitus;
for reducing the weight or preventing an increase of the weight or facilitating a reduction of the weight;
for preventing or treating the degeneration of pancreatic beta cells and/or for improving and/or restoring the functionality of pancreatic beta cells and/or restoring the functionality of pancreatic insulin secretion;
for preventing, slowing, delaying or treating diseases or conditions attributed to an abnormal accumulation of liver fat;
maintaining and/or improving the insulin sensitivity and/or for treating or preventing hyperinsulinemia and/or insulin resistance; or
preventing, slowing progression of delaying or treating athersclerosis and complications of atherosclerosis;
preventing, slowing progression of delaying or treating glaucoma and complications of glaucoma;
preventing, slowing progression of delaying or treating dyslipidemia/hyperlipidemia and complications of dyslipidemia/hyperlipidemia;
improving glycemic control in patients with type 2 diabetes as an adjunct to diet and exercise, or
improving glycemic control in patients with type 2 diabetes
in patients in need thereof characterized in that an inhibitor of 11-beta-hydroxysteroid dehydrogenase 1 of formula 1.a or 1.b as defined hereinafter is administered in combination or alternation with at least one second therapeutic agent 2 as defined hereinafter.

Furthermore the invention relates to methods
preventing, slowing progression of delaying or treating athersclerosis and complications of atherosclerosis; or
preventing, slowing progression of delaying or treating glaucoma and complications of glaucoma; or
preventing, slowing progression of delaying or treating dyslipidemia/hyperlipidemia and complications of dyslipidemia/hyperlipidemia
in patients in need thereof characterized in that an inhibitor of 11-beta-hydroxysteroid dehydrogenase 1 of formula 1.a or 1.b as defined hereinafter is administered to a patient in need thereof.

In addition the present invention relates to the use of an inhibitor of 11-beta-hydroxysteroid dehydrogenase 1 of formula 1.a or 1.b as defined hereinafter for the manufacture of a medicament for use in a method as described hereinbefore and hereinafter.

In addition the present invention relates to the use of at least one second therapeutic agent 2 as defined hereinafter for the manufacture of a medicament for use in a method as described hereinbefore and hereinafter.

The invention also relates to a use of a pharmaceutical composition according to this invention for use in a method as described hereinbefore and hereinafter.

BACKGROUND OF THE INVENTION

The compounds (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one (compound 1.a) and 3-{(S)-1-[4-(1-Cyclopropyl-2-oxo-1,2-dihydro-pyridin-4-yl)-phenyl]-ethyl}-(S)-6-(2-hydroxy-2-methyl-propyl)-6-phenyl-[1,3]oxazinan-2-one (compound 1.b), solvates, hydrates and pharmaceutically acceptable salts have been disclosed in WO 09/134,400 and WO 10/011,314 and have the following structure:

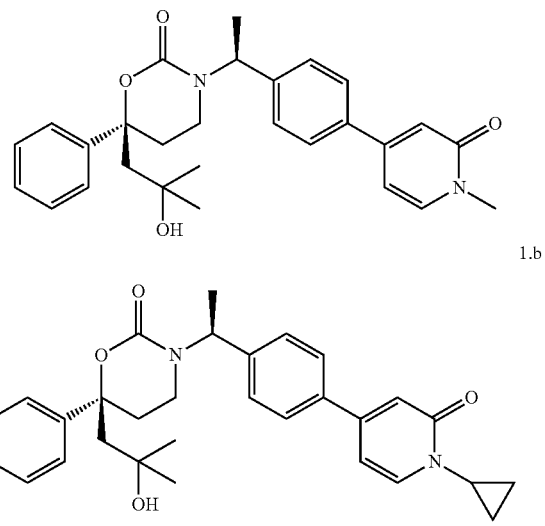

Compounds 1.a and 1.b are effective inhibitors of 11-beta-hydroxysteroid dehydrogenase 1 and are therefore promising therapeutic agents for ameliorating or treating disorders or diseases in which decreasing the level of cortisol is effective in treating a disease state.

Type 2 diabetes is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes is associated with a two to five fold increase in cardiovascular disease risk.

After long duration of disease, most patients with type 2 diabetes will eventually fail on oral therapy and become insulin dependent with the necessity for daily injections and multiple daily glucose measurements.

The UKPDS (United Kingdom Prospective Diabetes Study) demonstrated that intensive treatment with metformin, sulfonylureas or insulin resulted in only a limited improvement of glycemic control (difference in HbA1c ~0.9%). In addition, even in patients within the intensive treatment arm glycemic control deteriorated significantly over time and this was attributed to deterioration of β-cell function. Importantly, intensive treatment was not associated with a significant reduction in macrovascular complications, i.e. cardiovascular events.

Therefore there is an unmet medical need for methods, medicaments and pharmaceutical compositions with a good efficacy with regard to glycemic control, with regard to disease-modifying properties and with regard to reduction of cardiovascular morbidity and mortality while at the same time showing an improved safety profile.

AIM OF THE PRESENT INVENTION

The aim of the present invention is to provide a pharmaceutical composition and method for preventing, slowing progression of, delaying or treating a metabolic disorder.

A further aim of the present invention is to provide a pharmaceutical composition and method for improving glycemic control in a patient in need thereof.

Another aim of the present invention is to provide a pharmaceutical composition and method for preventing, slowing or delaying progression from impaired glucose tolerance (IGT), impaired fasting blood glucose (IFG), insulin resistance and/or metabolic syndrome to type 2 diabetes mellitus.

Yet another aim of the present invention is to provide a pharmaceutical composition and method for preventing, slowing progression of, delaying or treating of a condition or disorder from the group consisting of complications of diabetes mellitus.

A further aim of the present invention is to provide a pharmaceutical composition and method for reducing the weight or preventing an increase of the weight in a patient in need thereof.

Another aim of the present invention is to provide a new pharmaceutical composition with a high efficacy for the treatment of metabolic disorders, in particular of diabetes mellitus, impaired glucose tolerance (IGT), impaired fasting blood glucose (IFG), and/or hyperglycemia, which has good to very good pharmacological and/or pharmacokinetic and/or physicochemical properties.

A further aim of the present invention is to provide a pharmaceutical composition and method for preventing, slowing progression of delaying or treating athersclerosis and complications of atherosclerosis.

A further aim of the present invention is to provide a pharmaceutical composition and method for preventing, slowing progression of delaying or treating glaucoma and complications of glaucoma.

A further aim of the present invention is to provide a pharmaceutical composition and method for preventing, slowing progression of delaying or treating dyslipidemia/hyperlipidemia and complications of dyslipidemia/hyperlipidemia.

Further aims of the present invention become apparent to the one skilled in the art by description hereinbefore and in the following and by the examples.

SUMMARY OF THE INVENTION

Within the scope of the present invention it has now surprisingly been found that a pharmaceutical composition comprising compound 1.a and/or compound 1.b, solvates, hydrates or pharmaceutically acceptable salts thereof can advantageously be used in combination with at least one second therapeutic agent 2 which is suitable in the treatment or prevention of one or more conditions selected from type 1 diabetes mellitus, type 2 diabetes mellitus, impaired glucose tolerance (IGT), impaired fasting blood glucose (IFG) and hyperglycemia for preventing, slowing progression of, delaying or treating a metabolic disorder, in particular in improving glycemic control in patients. This opens up new therapeutic possibilities in the treatment and prevention of type 2 diabetes mellitus, overweight, obesity, complications of diabetes mellitus and of neighboring disease states.

Further also within the scope of the present invention is a pharmaceutical composition comprising compound 1.a and/or compound 1.b, solvates, hydrates or pharmaceutically acceptable salts thereof which can advantageously be used for preventing, slowing progression of delaying or treating athersclerosis and complications of atherosclerosis.

Further also within the scope of the present invention is a pharmaceutical composition comprising compound 1.a and/or compound 1.b, solvates, hydrates or pharmaceutically acceptable salts thereof which can advantageously be used for preventing, slowing progression of delaying or treating glaucoma and complications of glaucoma.

Further also within the scope of the present invention is a pharmaceutical composition comprising compound 1.a and/or compound 1.b, solvates, hydrates or pharmaceutically acceptable salts thereof which can advantageously be used for preventing, slowing progression of delaying or treating dyslipidemia/hyperlipidemia and complications of dyslipidemia/hyperlipidemia.

Further also within the scope of the present invention is a pharmaceutical composition comprising compound 1.a and/or compound 1.b, solvates, hydrates or pharmaceutically acceptable salts thereof which can advantageously be used in combination with at least one second therapeutic agent 2 for preventing, slowing progression of delaying or treating athersclerosis and complications of atherosclerosis.

Further also within the scope of the present invention is a pharmaceutical composition comprising compound 1.a and/or compound 1.b, solvates, hydrates or pharmaceutically acceptable salts thereof which can advantageously be used in combination with at least one second therapeutic agent 2 for preventing, slowing progression of delaying or treating glaucoma.

Further also within the scope of the present invention is a pharmaceutical composition comprising compound 1.a and/or compound 1.b, solvates, hydrates or pharmaceutically acceptable salts thereof which can advantageously be used in combination with at least one second therapeutic agent 2 for preventing, slowing progression of delaying or treating dyslipidemia/hyperlipidemia and complications of dyslipidemia/hyperlipidemia.

Further also within the scope of the present invention is a pharmaceutical composition comprising compound 1.a and/or compound 1.b, solvates, hydrates or pharmaceutically acceptable salts thereof which can advantageously be used in combination with at least one second therapeutic agent 2 as defined below and above, for improving glycemic control in patients with type 2 diabetes.

Further also within the scope of the present invention is a pharmaceutical composition comprising compound 1.a and/ or compound 1.b, solvates, hydrates or pharmaceutically acceptable salts thereof which can advantageously be used in combination with at least one second therapeutic agent 2 as defined below and above, as an adjunct to diet and exercise to improve glycemic control in patients with type 2 diabetes mellitus.

Therefore in a first aspect the present invention provides a pharmaceutical composition comprising a compound 1.a and/or a compound 1.b, solvates, hydrates or pharmaceutically acceptable salts thereof in combination with at least one second therapeutic agent 2 which is suitable in the treatment or prevention of one or more conditions selected from type 1 diabetes mellitus, type 2 diabetes mellitus, impaired glucose tolerance (IGT), impaired fasting blood glucose (IFG), hyperglycemia, dyslipidemia/hyperlipidemia.

According to another aspect of the invention there is provided a method for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity, metabolic syndrome, atherosclerosis, glaucoma, dyslipidemia/hyperlipidemia in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

According to another aspect of the invention there is provided a method for improving glycemic control and/or for reducing of fasting plasma glucose, of postprandial plasma glucose and/or of glycosylated hemoglobin HbA1c in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

According to another aspect of the invention there is provided a method for improving glycemic control in patients with type 2 diabetes in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

According to another aspect of the invention there is provided a method for improving glycemic control in patients with type 2 diabetes as an adjunct to diet and exercise in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

According to another aspect of the invention there is provided a method for slowing progression of delaying or treating atherosclerosis and complications of atherosclerosis in a patient in need thereof characterized in that a compound 1.a and/or a compound 1.b, solvates, hydrates or pharmaceutically acceptable salts thereof is/are administered to a patient in need thereof.

According to another aspect of the invention there is provided a method for slowing progression of delaying or treating glaucoma and complications of glaucoma in a patient in need thereof characterized in that a compound 1.a and/or a compound 1.b, solvates, hydrates or pharmaceutically acceptable salts thereof is/are administered to a patient in need thereof.

According to another aspect of the invention there is provided a method for slowing progression of delaying or treating dyslipidemia/hyperlipidemia and complications of dyslipidemia/hyperlipidemia to a patient in need thereof.

The pharmaceutical composition according to this invention may also have valuable disease-modifying properties with respect to diseases or conditions related to impaired glucose tolerance (IGT), impaired fasting blood glucose (IFG), insulin resistance, atherosclerosis, glaucoma, dyslipidemia/hyperlipidemia and/or metabolic syndrome.

According to another aspect of the invention there is provided a method for preventing, slowing, delaying or reversing progression from impaired glucose tolerance (IGT), impaired fasting blood glucose (IFG), insulin resistance and/or from metabolic syndrome to type 2 diabetes mellitus in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

As by the use of a pharmaceutical composition according to this invention an improvement of the glycemic control in patients in need thereof is obtainable, also those conditions and/or diseases related to or caused by an increased blood glucose level may be treated.

According to another aspect of the invention there is provided a method for preventing, slowing the progression of, delaying or treating of a condition or disorder selected from the group consisting of complications of diabetes mellitus such as glaucoma, cataracts and micro- and macrovascular diseases, such as nephropathy, retinopathy, neuropathy, tissue ischaemia, arteriosclerosis, myocardial infarction, stroke and peripheral arterial occlusive disease, in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter. The term "tissue ischaemia" particularly comprises diabetic macroangiopathy, diabetic microangiopathy, impaired wound healing and diabetic ulcer.

According to another aspect of the invention there is provided a method for reducing the weight or preventing an increase of the weight or facilitating a reduction of the weight in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

According to another aspect of the invention there is provided a method for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

By the administration of a combination or pharmaceutical composition according to the present invention an abnormal accumulation of fat in the liver may be reduced or inhibited. Therefore according to another aspect of the present invention there is provided a method for preventing, slowing, delaying or treating diseases or conditions attributed to an abnormal accumulation of liver fat in a patient in need thereof c characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

As a result thereof another aspect of the invention provides a method for maintaining and/or improving the insulin sensitivity and/or for treating or preventing hyperinsulinemia and/or insulin resistance in a patient in need thereof characterized in that a compound 1.a and/or a compound 1.b, solvates, hydrates or pharmaceutically acceptable salts thereof is/are administered in combination or alternation with at least one second therapeutic agent 2 as defined hereinbefore and hereinafter.

According to another aspect of the invention there is provided a compound 1.a and/or a compound 1.b, solvates, hydrates or pharmaceutically acceptable salts thereof for the use in preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or reducing the weight or preventing an increase of the weight or facilitating a reduction of the weight; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of liver fat; or maintaining and/or improving the insulin sensitivity and/or for treating or preventing hyperinsulinemia and/or insulin resistance; or preventing, slowing progression of delaying or treating athersclerosis and complications of atherosclerosis; or preventing, slowing progression of delaying or treating glaucoma and complications of glaucoma;

preventing, slowing progression of delaying or treating dyslipidemia/hyperlipidemia and complications of dyslipidemia/hyperlipidemia; or improving glycemic control in patients with type 2 diabetes as an adjunct to diet and exercise; or improving glycemic control in patients with type 2 diabetes in a patient in need thereof characterized in that the compound 1.a and/or a compound 1.b, solvates, hydrates or pharmaceutically acceptable salts thereof is administered in combination or alternation with at least one second therapeutic agent 2 as defined hereinbefore and hereinafter.

According to another aspect of the invention there is provided least one second therapeutic agent 2 as defined hereinbefore and hereinafter for the use in preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or reducing the weight or preventing an increase of the weight or facilitating a reduction of the weight; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of liver fat; or maintaining and/or improving the insulin sensitivity and/or for treating or preventing hyperinsulinemia and/or insulin resistance; or preventing, slowing progression of delaying or treating athersclerosis and complications of atherosclerosis; or preventing, slowing progression of delaying or treating glaucoma and complications of glaucoma;

preventing, slowing progression of delaying or treating dyslipidemia/hyperlipidemia and complications of dyslipidemia/hyperlipidemia;

improving glycemic control in patients with type 2 diabetes as an adjunct to diet and exercise; or improving glycemic control in patients with type 2 diabetes in a patient in need thereof characterized in that the least one second therapeutic agent 2 is administered in combination or alternation with compound 1.a and/or a compound 1.b, solvates, hydrates or pharmaceutically acceptable salts thereof.

According to another aspect of the invention there is provided a pharmaceutical composition according to the present invention for the use for a therapeutic and preventive method as described hereinbefore and hereinafter.

DEFINITIONS

The term "active ingredient" of a pharmaceutical composition according to the present invention means the compound 1.a and/or compound 1.b, solvates, hydrates or pharmaceutically acceptable salts thereof and/or the second therapeutic ingredient 2.

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 110 mg/dL (6.11 mmol/L). The word "fasting" has the usual meaning as a medical term.

The term "hyperglycemia" is defined as the condition in which a subject has a fasting blood glucose concentration above the normal range, greater than 110 mg/dL (6.11 mmol/L). The word "fasting" has the usual meaning as a medical term.

The term "hypoglycemia" is typically defined as a condition in which a subject has symptoms known to be caused by hypoglycaemia, i.e. low blood glucose concentration at the time the symptoms occur and reversal or improvement of symptoms or problems when the blood glucose concentration is restored to normal. Typically, plasma glucose levels below 70 mg/dl (3.9 mmol/L), in particular below 60 mg/dl (3.3 mmol/L), are considered hypoglycaemic.

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration greater than 110 mg/dL and less than 126 mg/dl (7.00 mmol/L).

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast.

The term "hyperinsulinemia" is defined as the condition in which a subject with insulin resistance, with or without euglycemia, in which the fasting or postprandial serum or plasma insulin concentration is elevated above that of normal, lean individuals without insulin resistance, having a waist-to-hip ration <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. In this method it is not possible to distinguish between hepatic and peripheral insulin resistance.

Furthermore insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$HOMA\text{-}IR=[\text{fasting serum insulin }(\mu U/mL)]\times[\text{fasting plasma glucose(mmol/L)}/22.5]$$

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected this is a particularly strong indication of the presence of prediabetes. Thus, it may be that in order to maintain glucose homoeostasis a person needs 2-3 times as much insulin as another person, without this having any direct pathological significance.

The methods to investigate the function of pancreatic beta-cells are similar to the above methods with regard to insulin sensitivity, hyperinsulinemia or insulin resistance: An improvement of the beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes. Insulin resistance can be confirmed in these individuals by calculating HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP≥130 or DBP≥85)
5. Fasting blood glucose ≥110 mg/dL The NCEP definitions have been validated (Laaksonen D E, et al. *Am J. Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

Within the meaning of the present invention glaucoma is a disease in which the optic nerve is damaged, leading to progressive, irreversible loss of vision. It is often, but not always, associated with increased pressure of the fluid in the eye. The nerve damage involves loss of retinal ganglion cells in a characteristic pattern. There are many different sub-types of glaucoma but they can all be considered a type of optic neuropathy. Raised intraocular pressure is a significant risk factor for developing glaucoma (above 21 mmHg or 2.8 kPa). One person may develop nerve damage at a relatively low pressure, while another person may have high eye pressure for years and yet never develop damage. Untreated glaucoma leads to permanent damage of the optic nerve and resultant visual field loss, which can progress to blindness.

Within the meaning of the present invention atherosclerosis (also known as arteriosclerotic vascular disease or ASVD) is a condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL), With the term "dyslipidemia/hyperlipidemia" a disorder of lipoprotein metabolism, including lipoprotein overproduction or deficiency is defined. Dyslipidemias may be manifested by elevation of the total cholesterol, the low-density lipoprotein (LDL) cholesterol and the triglyceride concentrations, and a decrease in the "good" high-density lipoprotein (HDL) cholesterol concentration in the blood. Dyslipidemia/hyperlipidemia within the meaning of the present invention is indicated when LDL cholesterol levels for adults more than 100 mg/dL (2.60 mmol/L), HDL cholesterol levels are equal to or lower than 40 mg/dL (1.02 mmol/L), and triglyceride levels are more than 150 mg/dL (1.7 mmol/L).

The terms "prophylactically treating" and "preventing" are used interchangeably.

DETAILED DESCRIPTION

The aspects according to the present invention, in particular the pharmaceutical compositions, methods and uses, refer to compound 1.a and/or compound 1.b, solvates, hydrates or pharmaceutically acceptable salts thereof.

The aspects according to the present invention, in particular the pharmaceutical compositions, methods and uses, refer to an at least one therapeutic agent 2 which is suitable in the treatment or prevention of one or more conditions selected from type 1 diabetes mellitus, type 2 diabetes mellitus, impaired glucose tolerance (IGT), impaired fasting blood glucose (IFG), atherosclerosis, glaucoma, dyslipidemia/hyperlipidemia and hyperglycemia.

Preferably the at least one second therapeutic agent 2 is selected from the groups 2.a) to 2.m) consisting of:
2.a) biguanides,
2.b) sulfonylureas,
2.c) metiglinides,
2.d) thiazolidindiones,
2.e) alpha-glucosidase inhibitors,
2.f) insulins and insulin analogues,
2.g) dipeptidyl peptidase IV inhibitors (DPP IV inhibitors)
2.h) SGLT 2 inhibitors,
2.i) PPAR gamma/alpha modulators,
2.j) glucose-dependent insulinotropic polypeptide agonists,
2.k) beta-3 agonists,
2.l) GLP1 and GLP1 analogues,
2.m) PPAR gamma modulators, and
2.n) HMG-CoA reductase inhibitors
2.o) PPAR delta modulators.

More preferably the at least one second therapeutic agent 2 is selected from the groups 2.a), 2.g) and 2.h) as described hereinbefore and hereinafter.

Examples of biguanides are metformin (2.a1), phenformin (2.a2) and buformin (2.a3). Compound 1.a and/or a compound 1.b, solvates, hydrates or pharmaceutically acceptable salts thereof in combination with a biguanide, for example with metformin, can improve glycemic control and may act synergistically with the biguanide, for example to reduce weight that has overall beneficial effects on the metabolic syndrome which is commonly associated with type 2 diabetes mellitus.

Examples of sulfonylureas are chlorpropamide (2.b1), acetohexamide (2.b2), tolazamide (2.b3), glibenclamide (2.b4), tolbutamide (2.b5), glimepiride (2.b6), glipizide (2.b7), gliquidone (2.b8), glibornurid (2.b9), glyburide (2.b10) and gliclazide (2.b11). As the efficacy of sulfonylureas wears off over the course of treatment, a combination of compound 1.a and/or compound 1.b, solvates, hydrates or pharmaceutically acceptable salts thereof with a sulfonylurea may offer additional benefit to the patient in terms of better glycemic control. This combination may also allow a reduction in the dose of sulfonylureas which may translate into less hypoglycemia which is an undesirable side effect of sulfonylureas.

Examples of meglitinides are nateglinide (2.c1), repaglinide (2.c2) and mitiglinide (2.c3). As the efficacy of meglitinides wears off over the course of treatment, a combination of compound 1.a and/or compound 1.b, solvates, hydrates or pharmaceutically acceptable salts thereof with a meglitinide may offer additional benefit to the patient in terms of better glycemic control. This combination may also allow a reduction in the dose of meglitinides which may translate into less hypoglycemia which is an undesirable side effect of meglitinides.

Examples of thiazolidindiones are pioglitazone (2.d1), rosiglitazone (2.d2), troglitazone (2.d3) and ciglitazone (2.d4). Additional benefits from the combination of compound 1.a and/or compound 1.b, solvates, hydrates or pharmaceutically acceptable salts thereof and a thiazolidindione may relate to synergistic reduction in blood glucose, an improved glycemic control, an improvement of fluid retention caused by thiazolidindiones and reducing or nullifying weight gain associated with the use of thiazolidindiones.

Examples of alpha-glucosidase inhibitors are miglitol (2.e1), acarbose (2.e2) and voglibose (2.e3). A combination of compound 1.a and/or compound 1.b, solvates, hydrates or pharmaceutically acceptable salts thereof and an alpha-glucosidase inhibitor will add to their blood glucose lowering effect and may allow a reduction in the dose of the alpha-glucosidase inhibitor that are commonly associated with unpleasant gastro-intestinal side effects, thereby making it more tolerable and improve the patients compliance with the treatment.

Examples of insulins and insulin analogues are short acting insulins like insulin lispro (Humalog®) (2.f1), insulin aspartat (Novorapid®) (2.f2), insulin glulisine (Apidra®) (2.f3), regular insulin (2.f4), intermediate acting insulins like NPH-insulins and long acting insulins like lente (2.f5) and ultralente insulin (2.f6), insulin glargine (Lantus®) (2.f7), insulin detemir (Levemir®) (2.f8). The term insulins includes recombinant insulins. The use of insulin is commonly associated with weight gain as a result of the anabolic effects of insulin as well as fluid retention. Combining compound 1.a and/or compound 1.b, solvates, hydrates or pharmaceutically acceptable salts thereof with insulin or an insulin analogue will achieve a better glycemic control with lower doses of insulin.

Examples of DPP IV inhibitors are denagliptin (2.g1), carmegliptin (2.g2), melogliptin (2.g3) sitagliptin (2.g4), vildagliptin (2.g5), saxagliptin (2.g6), linagliptin (2.g7), dutogliptin (2.g8), gemigliptin (2.g9) and alogliptin (2.g10). Combining compound 1.a and/or compound 1.b, solvates, hydrates or pharmaceutically acceptable salts thereof with a DPP IV inhibitor is expected to improve glycemic control.

Examples of SGLT 2 inhibitors are 6-(4-ethylbenzyl)-4-(β-D-glucopyranos-1-yl)-2-methoxy-benzonitrile (2.h1), 2-(4-ethylbenzyl)-4-(β-D-glucopyranos-1-yl)-5-methoxy-benzonitrile (2.h2), 1-cyano-2-(4-ethylbenzyl)-4-(β-D-glucopyranos-1-yl)-5-methyl-benzene (2.h3), 2-(4-ethylbenzyl)-4-(β-D-glucopyranos-1-yl)-5-hydroxy-benzonitrile (2.h4), 2-(4-ethyl-benzyl)-4-(β-D-glucopyranos-1-yl)-benzonitrile (2.h5), 2-(4-cyclopropyl-benzyl)-4-(β-D-glucopyranos-1-yl)-benzonitrile (2.h6), 1-chloro-4-(β-D-glucopyranos-1-yl)-2-(4-ethynyl-benzyl)-benzene (2.h7), 1-chloro-4-(β-D-glucopyranos-1-yl)-2-[4-((R)-tetrahydrofuran-3-yloxy)-benzyl]-benzene (2.h8), 1-chloro-4-(β-D- glucopyranos-1-yl)-2-[4-((S)-tetrahydrofuran-3-yloxy)-benzyl]-benzene (2.h9), 1-methyl-2-[4-((R)-tetrahydrofuran-3-yloxy)-benzyl]-4-(β-D-glucopyranos-1-yl)-benzene (2.h10), 1-methyl-2-[4-((S)-tetrahydrofuran-3-yloxy)-benzyl]-4-(β-D-glucopyranos-1-yl)-benzene (2.h11), dapagliflozin (2.h12), atigliflozin (2.h13), remogliflozin (2.h14), sergliflozin (2.h15) and canagliflozin (2.h16). Combining compound 1.a and/or compound 1.b, solvates, hydrates or pharmaceutically acceptable salts thereof with a SGLT 2 inhibitor is expected to improve glycemic control.

Compounds (2.h1) to (2.h11) and methods of their synthesis are described for example in the following patent applications: WO 2005/092877, WO 2006/117360, WO 2006/117359, WO 2006/120208, WO 2006/064033, WO 2007/031548, WO 2007/093610, WO 2008/020011, WO 2008/055870.

Examples of PPAR gamma/alpha modulators are tesaglitazar (2.i1), muraglitazar (2.i2) and KRP297 (2.i3). Combining compound 1.a and/or compound 1.b, solvates, hydrates or pharmaceutically acceptable salts thereof with a PPAR gamma/alpha modulator is expected to improve glycemic control.

Examples of glucose-dependent insulinotropic polypeptide agonists are pramlintide (2.j1) and amlyin (2.j2). Combinations with such second therapeutic agents 2 are expected to improve glycemic control.

Examples of beta-3 agonists are ritobegron (2.k1), YM 178 (2.k2), solabegron (2.k3), talibegronb (2.k4), N-5984 (2.k5), GRC-1087 (2.k6), rafabegron (2.k7) and FMP825 (2.k8). Combining compound 1.a and/or compound 1.b, solvates, hydrates or pharmaceutically acceptable salts thereof with a beta-3 agonist is expected to improve glycemic control.

An example of GLP1 and GLP1 analogues is exenatide (2.l1), liraglutide (2.l2) and taspoglutide (2.l3). Combining compound 1.a and/or compound 1.b, solvates, hydrates or pharmaceutically acceptable salts thereof with a GLP-1 analogue is expected to improve glycemic control and add to GLP-1 analogue weight reducing effect.

An example of PPAR gamma modulators is metaglidasen (2.m1). Combining a compound 1.a and/or compound 1.b, solvates, hydrates or pharmaceutically acceptable salts thereof with a PPAR gamma modulator is expected to improve glycemic control.

Examples of HMG-CoA reductase inhibitors are simvastatin (2.n1), lovastatin (2.n2), and provastatin (2.n3). Combining compound 1.a and/or compound 1.b, solvates, hydrates or pharmaceutically acceptable salts thereof with a HMG-CoA reductase inhibitor is expected to improve glycemic control.

Examples of PPAR delta modulators are GW 501516 (2.o1), GW 0742 (2.o2), L165041 (2.o3), LY 465608 (2.o4), and L-796449 (2.o5).

Even more preferably the at least one second therapeutic agent 2 is selected from the group consisting of (2.a1), (2.d1), (2.g7) and (2.h9).

Most preferably the at least one second therapeutic agent 2 is selected from the group consisting of consisting of (2.a1), (2.g7), (2.h9).

In addition, therapeutic agents 2 can also be selected from GPR119 agonists.

According to this invention it is to be understood that the definitions of the above listed second therapeutic agents 2 also comprise their pharmaceutically acceptable salts as well as hydrates, solvates and polymorphic forms thereof.

Therefore the pharmaceutical compositions, methods and uses according to this invention relate to combinations which are selected from the Table 1.

TABLE 1

| Composition No. | Compound 1 | Second therapeutic agent 2 |
|---|---|---|
| 1 | 1.a | 2.a1 |
| 2 | 1.a | 2.a2 |
| 3 | 1.a | 2.a3 |
| 4 | 1.a | 2.b1 |
| 5 | 1.a | 2.b2 |
| 6 | 1.a | 2.b3 |
| 7 | 1.a | 2.b4 |
| 8 | 1.a | 2.b5 |
| 9 | 1.a | 2.b6 |
| 10 | 1.a | 2.b7 |
| 11 | 1.a | 2.b8 |
| 12 | 1.a | 2.b9 |
| 13 | 1.a | 2.b10 |
| 14 | 1.a | 2.b11 |
| 15 | 1.a | 2.c1 |
| 16 | 1.a | 2.c2 |
| 17 | 1.a | 2.c3 |
| 18 | 1.a | 2.d1 |
| 19 | 1.a | 2.d2 |
| 20 | 1.a | 2.d3 |
| 21 | 1.a | 2.d4 |
| 22 | 1.a | 2.e1 |
| 23 | 1.a | 2.e2 |
| 24 | 1.a | 2.e3 |
| 25 | 1.a | 2.f1 |
| 26 | 1.a | 2.f2 |
| 27 | 1.a | 2.f3 |
| 28 | 1.a | 2.f4 |
| 29 | 1.a | 2.f5 |
| 30 | 1.a | 2.f6 |
| 31 | 1.a | 2.f7 |
| 32 | 1.a | 2.f8 |
| 33 | 1.a | 2.g1 |
| 34 | 1.a | 2.g2 |
| 35 | 1.a | 2.g3 |
| 36 | 1.a | 2.g4 |
| 37 | 1.a | 2.g5 |
| 38 | 1.a | 2.g6 |
| 39 | 1.a | 2.g7 |
| 40 | 1.a | 2.g8 |
| 41 | 1.a | 2.g9 |
| 42 | 1.a | 2.g10 |
| 43 | 1.a | 2.h1 |
| 44 | 1.a | 2.h2 |
| 45 | 1.a | 2.h3 |
| 46 | 1.a | 2.h4 |
| 47 | 1.a | 2.h5 |
| 48 | 1.a | 2.h6 |
| 49 | 1.a | 2.h7 |
| 50 | 1.a | 2.h8 |
| 51 | 1.a | 2.h9 |
| 52 | 1.a | 2.h10 |
| 53 | 1.a | 2.h11 |
| 54 | 1.a | 2.h12 |
| 55 | 1.a | 2.h13 |
| 56 | 1.a | 2.h14 |
| 57 | 1.a | 2.h15 |
| 58 | 1.a | 2.h16 |
| 59 | 1.a | 2.i1 |
| 60 | 1.a | 2.i2 |
| 61 | 1.a | 2.i3 |
| 62 | 1.a | 2.j1 |
| 63 | 1.a | 2.j2 |
| 64 | 1.a | 2.k1 |
| 65 | 1.a | 2.k2 |
| 66 | 1.a | 2.k3 |
| 67 | 1.a | 2.k4 |
| 68 | 1.a | 2.k5 |
| 69 | 1.a | 2.k6 |
| 70 | 1.a | 2.k7 |
| 71 | 1.a | 2.k8 |

TABLE 1-continued

| Composition No. | Compound 1 | Second therapeutic agent 2 |
|---|---|---|
| 72 | 1.a | 2.l1 |
| 73 | 1.a | 2.l2 |
| 74 | 1.a | 2.l3 |
| 75 | 1.a | 2.m1 |
| 76 | 1.a | 2.n1 |
| 77 | 1.a | 2.n2 |
| 78 | 1.a | 2.n3 |
| 79 | 1.a | 2.o1 |
| 80 | 1.a | 2.o2 |
| 81 | 1.a | 2.o3 |
| 82 | 1.a | 2.o4 |
| 83 | 1.a | 2.o5 |
| 84 | 1.b | 2.a1 |
| 85 | 1.b | 2.a2 |
| 86 | 1.b | 2.a3 |
| 87 | 1.b | 2.b1 |
| 88 | 1.b | 2.b2 |
| 89 | 1.b | 2.b3 |
| 90 | 1.b | 2.b4 |
| 91 | 1.b | 2.b5 |
| 92 | 1.b | 2.b6 |
| 93 | 1.b | 2.b7 |
| 94 | 1.b | 2.b8 |
| 95 | 1.b | 2.b9 |
| 96 | 1.b | 2.b10 |
| 97 | 1.b | 2.b11 |
| 98 | 1.b | 2.c1 |
| 99 | 1.b | 2.c2 |
| 100 | 1.b | 2.c3 |
| 101 | 1.b | 2.d1 |
| 102 | 1.b | 2.d2 |
| 103 | 1.b | 2.d3 |
| 104 | 1.b | 2.d4 |
| 105 | 1.b | 2.e1 |
| 106 | 1.b | 2.e2 |
| 107 | 1.b | 2.e3 |
| 108 | 1.b | 2.f1 |
| 109 | 1.b | 2.f2 |
| 110 | 1.b | 2.f3 |
| 111 | 1.b | 2.f4 |
| 112 | 1.b | 2.f5 |
| 113 | 1.b | 2.f6 |
| 114 | 1.b | 2.f7 |
| 115 | 1.b | 2.f8 |
| 116 | 1.b | 2.g1 |
| 117 | 1.b | 2.g2 |
| 118 | 1.b | 2.g3 |
| 119 | 1.b | 2.g4 |
| 120 | 1.b | 2.g5 |
| 121 | 1.b | 2.g6 |
| 122 | 1.b | 2.g7 |
| 123 | 1.b | 2.g8 |
| 124 | 1.b | 2.g9 |
| 125 | 1.b | 2.g10 |
| 126 | 1.b | 2.h1 |
| 127 | 1.b | 2.h2 |
| 128 | 1.b | 2.h3 |
| 129 | 1.b | 2.h4 |
| 130 | 1.b | 2.h5 |
| 131 | 1.b | 2.h6 |
| 132 | 1.b | 2.h7 |
| 133 | 1.b | 2.h8 |
| 134 | 1.b | 2.h9 |
| 135 | 1.b | 2.h10 |
| 136 | 1.b | 2.h11 |
| 137 | 1.b | 2.h12 |
| 138 | 1.b | 2.h13 |
| 139 | 1.b | 2.h14 |
| 140 | 1.b | 2.h15 |
| 141 | 1.b | 2.h16 |
| 142 | 1.b | 2.i1 |
| 143 | 1.b | 2.i2 |
| 144 | 1.b | 2.i3 |
| 145 | 1.b | 2.j1 |
| 146 | 1.b | 2.j2 |
| 147 | 1.b | 2.k1 |
| 148 | 1.b | 2.k2 |
| 149 | 1.b | 2.k3 |
| 150 | 1.b | 2.k4 |
| 151 | 1.b | 2.k5 |
| 152 | 1.b | 2.k6 |
| 153 | 1.b | 2.k7 |
| 154 | 1.b | 2.k8 |
| 155 | 1.b | 2.l1 |
| 156 | 1.b | 2.l2 |
| 157 | 1.b | 2.l3 |
| 158 | 1.b | 2.m1 |
| 159 | 1.b | 2.n1 |
| 160 | 1.b | 2.n2 |
| 161 | 1.b | 2.n3 |
| 162 | 1.b | 2.o1 |
| 163 | 1.b | 2.o2 |
| 164 | 1.b | 2.o3 |
| 165 | 1.b | 2.o4 |
| 166 | 1.b | 2.o5 |

When this invention refers to patients requiring treatment or prevention, it relates primarily to treatment and prevention in humans, but the pharmaceutical composition may also be used accordingly in veterinary medicine on mammals.

As described hereinbefore by the administration of the pharmaceutical composition according to this invention and in particular in view of the activity of compound 1.a and 1.b therein, the intracellular cortisol level is reduced resulting in improved insulin sensitivity and glucose control. Therefore a treatment or prophylaxis according to this invention is advantageously suitable in those patients in need of such treatment or prophylaxis who are diagnosed of one or more of the conditions selected from the group consisting of overweight, class I obesity, class II obesity, class III obesity, visceral obesity and abdominal obesity or for those individuals in which a weight increase is contraindicated.

The pharmaceutical composition according to this invention and in particular compound 1.a and 1.b therein exhibits a very good efficacy with regard to glycemic control, in particular in view of a reduction of fasting plasma glucose, postprandial plasma glucose and/or glycosylated hemoglobin (HbA1c).

Furthermore the method and/or use according to this invention is advantageously applicable in those patients who show one, two or more of the following conditions:

(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 8.0%.

The present invention also discloses the use of the pharmaceutical composition for improving glycemic control in patients having type 2 diabetes or showing first signs of pre-diabetes. Thus, the invention also includes diabetes prevention. If therefore a pharmaceutical composition according to this invention is used to improve the glycemic control as soon as one of the above-mentioned signs of prediabetes is present, the onset of manifest type 2 diabetes mellitus can be delayed or prevented.

Furthermore the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

It can be found that by using a pharmaceutical composition according to this invention an improvement of the glycemic control can be achieved even in those patients who have insufficient glycemic control in particular despite treatment with an antidiabetic drug, for example despite maximal tolerated dose of oral monotherapy with either metformin or an antidiabetic of the class of sulphonylureas. A maximal tolerated dose with regard to metformin is for example 850 mg three times a day or any equivalent thereof. In the scope of the present invention the term "insufficient glycemic control" means a condition wherein patients show HbA1c values above 6.5%, in particular above 8%.

Therefore according to a preferred embodiment of the present invention there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that compound 1.a and/or compound 1.b, solvates, hydrates or pharmaceutically acceptable salts thereof as defined hereinbefore is administered in combination or alternation with at least one second therapeutic agent 2 as defined hereinbefore and hereinafter.

Furthermore a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL,
(f) LDL-cholesterol blood levels ≥130 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

With a pharmaceutical composition according to this invention treatment or prophylaxis according to this invention may be advantageous possible in those patients for which the mono-therapy with another antidiabetic drug, such as for example metformin, is contraindicated and/or who have an intolerance against such drugs at therapeutic doses. In particular a treatment or prophylaxis according to this invention may be advantageous possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore it may be found that the administration of a pharmaceutical composition according to this invention results in no risk or in a low risk of hypoglycemia. Therefore a treatment or prophylaxis according to this invention may also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

Administration of compound 1.a and/or compound 1.b, solvates, hydrates or pharmaceutically acceptable salts thereof according to this invention in combination with at least one second therapeutic agent 2 can have an additive or over-additive effect and provide for dose reduction, side-effect reduction and/or interval extension when compared to the individual compound 1.a and/or compound 1.b or to the individual second therapeutic agent 2 used in monotherapy in the usual way. The effects mentioned above are observed both when compound 1.a and/or compound 1.b and the second therapeutic agent 2 are administered in combination, for example simultaneously, and when they are administered in alternation, for example successively in separate formulations. In the case of the second therapeutic agent being an injectable, especially a biological agent, other benefits of a combination with the compound 1.a and/or compound 1.b may be seen, as for example, cost reduction by way of interval and/or dose reduction.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general however the compound 1.a and/or compound 1.b according to this invention, and the at least one second therapeutic agent 2 are included in the pharmaceutical composition or dosage form in an amount sufficient that by their administration in combination or alternation the glycemic control in the patient to be treated is improved.

In the following preferred ranges of the amount of compound 1.a and/or compound 1.b and of the second therapeutic agent 2 to be employed in the pharmaceutical composition and the methods and uses according to this invention are described. These ranges refer to the amounts to be administered per day with respect to an adult patient and can be adapted accordingly with regard to an administration 2, 3, 4 or more times daily and with regard to other routes of administration and with regard to the age of the patient.

Within the scope of the present invention the pharmaceutical composition (with the exception of insulins and GLP-1 agonists) is preferably administered orally. Other forms of administration are possible and described hereinafter. Preferably the dosage form comprising the compound 1.a and/or compound 1.b is administered orally. The route of administration of the $2^{nd}$ therapeutic agent is usually well known.

In general the amount of the compound 1.a and/or compound 1.b in the pharmaceutical composition and methods according to this invention is preferably in the range from 1/10 to 1/1 of the amount usually recommended for a monotherapy using said compounds. Advantageously, the combination therapy according to the present invention utilizes lower dosages of the individual compound 1.a and compound 1.b or of the individual second therapeutic agent 2 used in monotherapy or used in conventional therapeutics, thus avoiding possible toxicity and adverse side effects incurred when those agents are used as monotherapies.

The amount of compound 1.a and compound 1.b is preferably in the range from 0.1 mg to 1000 mg or 0.1 to 100 mg, even more preferably from 1 to 50 mg or 2 to 50 mg per day. The oral administration is preferred. Therefore a pharmaceutical composition may comprise the hereinbefore mentioned amounts for once daily administration and from 0.05 mg to 500 mg, even more preferably from 0.05 to 50 mg or 0.5 to 25 mg for twice daily administration.

In general the amount of the second therapeutic agent 2 in the pharmaceutical composition and methods according to this invention is preferably in the range from 1/5 to 1/1 of the amount usually recommended for a monotherapy using said second therapeutic agent.

A preferred dosage range of metformin is 100 to 4000 mg, in particular 200 to 3500 mg, most preferably 500 to 3000 mg per day. The preferred range of amounts in the pharmaceutical composition for an administration once, twice or three times daily is 100 to 3000, 50 to 1500 and 35 to 1000 mg respectively. Examples are 500 or 850 mg once, twice or three times daily, 1000 mg once or twice daily or 2000 mg once daily.

A preferred dosage range of pioglitazone is 5 to 50 mg per day. The preferred range of amounts in the pharmaceutical composition for an administration once, twice or three times daily is 5 to 50, 2 to 25 and 2 to 20 mg respectively. Examples are 15, 30 or 45 mg once daily.

A preferred dosage range of a rosiglitazone is 1 mg to 10 mg per day. The preferred range of amounts in the pharmaceutical composition for an administration once or twice times daily is 4 to 8 mg and 4 mg respectively.

A preferred dosage range of a thiazolidindione (other than pioglitazone or rosiglitazone as described above) is 2 to 100 mg per day. The preferred range of amounts in the pharmaceutical composition for an administration once, twice or three times daily is 2 to 100, 1 to 50 and 1 to 33 mg respectively.

A preferred dosage range of miglitol is 10 to 300 mg per day. The preferred range of amounts in the pharmaceutical composition for an administration once, twice or three times daily is 10 to 300, 5 to 150 and 3 to 100 mg respectively. Examples are 50 or 100 mg once, twice or three times daily.

A preferred dosage range of glibenclamide is 1 to 20 mg per day. The preferred range of amounts in the pharmaceutical composition for an administration once, twice or three times daily is 1 to 20, 0.5 to 10 and 0.5 to 7 mg respectively.

A preferred dosage range of tolbutamide is 100 to 3000 mg, preferably 500 to 3000 mg per day. The preferred range of amounts in the pharmaceutical composition for an administration once, twice or three times daily is 100 to 3000, 50 to 1500 and 35 to 1000 mg respectively.

A preferred dosage range of glimepiride is 0.5 to 10 mg, in particular 1 to 6 mg per day. The preferred range of amounts in the pharmaceutical composition for an administration once, twice or three times daily is 0.5 to 10, 0.25 to 5 and 0.2 to 3 mg respectively.

A preferred dosage range of glipizid is 1 to 50 mg, in particular 2.5 to 40 mg per day. The preferred range of amounts in the pharmaceutical composition for an administration once, twice or three times daily is 1 to 50, 0.5 to 25 and 0.3 to 17 mg respectively.

A preferred dosage range of gliquidon is 10 to 150 mg, in particular 30 to 120 mg per day. The preferred range of amounts in the pharmaceutical composition for an administration once, twice or three times daily is 10 to 150, 5 to 75 and 3 to 50 mg respectively.

A preferred dosage range of glibornurid is 5 to 75 mg per day. The preferred range of amounts in the pharmaceutical composition for an administration once, twice or three times daily is 5 to 75, 3 to 40 and 2 to 25 mg respectively.

A preferred dosage range of gliclazid is 25 to 320 mg, in particular 80 to 160 mg per day. The preferred range of amounts in the pharmaceutical composition for an administration once, twice or three times daily is 25 to 320, 12 to 160 and 10 to 80 mg respectively.

A preferred dosage range of nateglinide is 15 to 540 mg, in particular 60 to 360 mg per day. The preferred range of amounts in the pharmaceutical composition for an administration once, twice or three times daily is 15 to 360, 7 to 180 and 5 to 120 mg respectively.

A preferred dosage range of repaglinide is 0.1 to 16 mg, in particular 0.5 to 12 mg per day. The preferred range of amounts in the pharmaceutical composition for an administration once, twice or three times daily is 0.1 to 16, 0.05 to 8 and 0.03 to 5 mg respectively.

A preferred dosage range of metaglidasen is 40 to 600 mg, in particular 200 to 600 mg per day. The preferred range of amounts in the pharmaceutical composition for an administration once, twice or three times daily is 40 to 600, 20 to 300 and 15 to 200 mg respectively.

A preferred dosage range of a PPAR gamma/alpha modulator is 0.5 to 10 mg, in particular 2.5 to 5 mg per day. The preferred range of amounts in the pharmaceutical composition for an administration once, twice or three times daily is 0.5 to 10, 0.2 to 5 and 0.1 to 3 mg respectively.

A preferred dosage range of a pramlintide is 15 µg to 120 µg per day. The preferred range of amounts in the pharmaceutical composition for an administration once, twice or three times daily is 15 to 120, 8 to 60 and 5 to 40 µg respectively.

A preferred dosage range of an alpha glucosidase inhibitor is 0.1 to 500 mg per day. The preferred range of amounts in the pharmaceutical composition for an administration once, twice or three times daily is 0.1 to 500, 0.05 to 250 and 0.03 to 133 mg respectively.

A preferred dosage range of a voglibose is 0.1 to 2.0 mg per day, in particular 0.2 to 1.0 mg per day. The preferred range of amounts in the pharmaceutical composition for an administration twice or three times daily is 0.1 to 0.5 and 0.1 to 0.3 mg respectively.

A preferred dosage range of a acarbose is 50 to 300 mg per day, in particular 150 to 300 mg per day. The preferred range of amounts in the pharmaceutical composition for an administration twice or three times daily is 100 to 150 and 50 to 100 mg respectively. Examples are 50 or 100 mg twice or three times daily.

A preferred dosage range of a insulin is 1 to 250 IU per day. The preferred range of amounts in the pharmaceutical composition for an administration once, twice or three times daily is 1 to 250, 0.5 to 125 and 0.3 to 90 IU respectively. The term "IU" means international units.

A preferred dosage range of a linagliptine is 1 to 10 mg per day, in particular 3 to 6 mg per day. The preferred range of amounts in the pharmaceutical composition for an administration twice or three times daily is 1 to 5 and 2 to 3 mg respectively.

A preferred dosage range of a compound of group 2.h) is 1 to 100 mg per day, in particular 5 to 50 mg per day more preferably 10 to 25 mg. The preferred range of amounts in the pharmaceutical composition for an administration twice or three times daily is 5 to 50 and 10 to 25 mg respectively.

The amount of 1.a and/or 1.b and of the second therapeutic agent 2 in the pharmaceutical composition according to this invention correspond to the respective dosage ranges as provided hereinbefore. For example a pharmaceutical composition comprises an amount of 2.5 to 100 mg of 1.a and/or 1.b and metformin in an amount of 50 to 1500 mg.

In the methods and uses according to the present invention 1.a and/or 1.b and the at least one second therapeutic 2 ingredient are administered in combination or alternation. The term "administration in combination" means that both active ingredients are administered at the same time, i.e. simultaneously, or essentially at the same time. The term "administration in alternation" means that at first a first active ingredient is administered and after a period of time the second active ingredient is administered, i.e. both active ingredients are administered sequentially. The period of time may be in the range from 30 min to 12 hours. The administration which is in combination or in alternation may be once, twice, three times or four times daily.

With regard to the administration of 1.a and/or 1.b in combination with the at least one second therapeutic ingredient 2 all active ingredients may be present in a single dosage form, for example in a tablet or capsule, or each active ingredient may be present in a separate dosage form, for example in two different or identical dosage forms.

With regard to their administration in alternation each of the active ingredients is present in a separate dosage form, for example in two different or identical dosage forms.

Therefore the pharmaceutical composition according to this invention may be present as single dosage forms which comprise both 1.a and/or 1.b and the at least one second therapeutic ingredient 2 as well as separate dosage forms wherein one dosage form comprises 1.a and/or 1.b and the other dosage form comprises the at least one second therapeutic ingredient 2.

The case may arise in which one active ingredient has to be administered more often, for example twice per day, than the other active ingredient, which for example needs administration once daily. Therefore the term "administration in combination or alternation" also includes an administration scheme in which first both active ingredients are administered in combination or alternation and after a period of time only one active ingredient is administered again or vice versa.

Therefore the present invention also includes pharmaceutical compositions which are present a separate dosage forms wherein one dosage form comprises 1.a and/or 1.b and the second therapeutic agent 2 and the other dosage form comprises either 1.a and/or 1.b or the at least one second therapeutic agent 2.

A pharmaceutical composition which is present as a separate or multiple dosage form, preferably as a kit of parts, is useful in combination therapy to flexibly suit the individual therapeutic needs of the patient.

A preferred kit of parts comprises
(a) a first containment containing a dosage form comprising 1.a and/or 1.b and at least one pharmaceutically acceptable carrier, and
(b) a second containment containing a dosage form comprising the at least one second therapeutic agent 2 and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered in combination or alternation.

A yet further aspect of the present invention is a manufacture comprising a medicament which comprises 1.a and/or 1.b according to the present invention and a label or package insert which comprises instructions that the medicament may or is to be administered in combination or alternation with a medicament comprising at least one second therapeutic agent 2 according to the present invention.

Another further aspect of the present invention is a manufacture comprising a medicament which comprises at least one second therapeutic agent 2 according to the present invention and a label or package insert which comprises instructions that the medicament may or is to be administered in combination or alternation with a medicament comprising 1.a and/or 1.b according to the present invention.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, sub-cutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers which must be "acceptable" in the sense of being compatible with the other ingredients of the formulation and not deleterious to the recipient thereof.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

The pharmaceutical compositions and methods according to this invention show advantageous effects in the treatment and prevention of those diseases and conditions as described hereinbefore compared with pharmaceutical compositions and methods which comprise only one of both active ingredients. Advantageous effect may be seen for example with respect to efficacy, dosage strength, dosage frequency, pharmacodynamic properties, pharmacokinetic properties, adverse effects, etc.

Any of the above mentioned combinations within the scope of the invention may be tested by animal models known in the art. In the following in vivo experiments are described which are suitable to evaluate pharmacologically relevant properties of pharmaceutical compositions and methods according to this invention:

Pharmaceutical compositions and methods according to this invention can be tested in hyperinsulinemic or diabetic non-human primates.

The effect on glycemic control of the combinations according to this invention can be tested after single or multiple dosing of 1.a and/or 1.b and a second therapeutic agent 2 alone and in combination in the animal models described hereinbefore by following mean fasting plasma glucose. The combinations according to the present invention significantly reduce mean fasting glucose compared to each monotherapy. In addition, after multiple dosing of 1.a and/or 1.b and a second therapeutic agent 2 alone and in combination in the animal models described hereinbefore, the effect on glycemic control can be determined by measuring the HbA1c or fructosamine values in blood. The combinations according to this invention significantly reduce HbA1c or fructosamine compared to each monotherapy.

The possible dose reduction of either 1.a and/or 1.b or the second therapeutic agent 2 or of both active ingredients can be tested by the effect on glycemic control of lower doses of the combinations and monotherapies in the animal models described hereinbefore. The combinations according to this invention at the lower doses significantly improve glycemic control compared to placebo treatment whereas the monotherapies at lower doses do not.

Examples of pharmaceutically acceptable carriers are known to the one skilled in the art.

Methods for the manufacture of 1.a and/or 1.b according to this invention are known to the one skilled in the art. The compounds according to this invention can be prepared using synthetic methods as described in the literature, in particular as described in WO 09/134,400 and WO 10/011,314.

The methods of synthesis for the second therapeutic agent 2 are described in the scientific literature and/or in published patent documents.

1.a and/or 1.b and/or the second therapeutic agent 2 may be present in the form of a pharmaceutically acceptable salt. Pharmaceutically acceptable salts include such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

1.a and/or 1.b and/or the second therapeutic agent 2 or a pharmaceutically acceptable salt thereof may be present in the form of a solvate such as a hydrate or alcohol adduct.

The biological properties of 1.a and/or 1.b may be investigated as it is described for example in WO 09/134,400 and WO 10/011,314.

EXAMPLES OF FORMULATIONS

The following examples of formulations, which may be obtained analogously to methods known in the art, serve to illustrate the present invention more fully without restricting it to the contents of these examples. The term "active substance" denotes one or more compounds according to the invention, i.e. denotes 1.a and/or 1.b according to this invention or a second therapeutic agent 2 according to this invention or a combination of 1.a and/or 1.b with said second therapeutic agent 2, for example selected from the combinations 1a to 7h as listed in Table 1. Additional suitable formulations for the second therapeutic agent 2 may be those formulations which are available on the market or formulations described in the literature, for example as disclosed in current issues of "Rote Liste®" (Editio Cantor Verlag Aulendorf, Germany) or of "Physician's Desk Reference".

Example 1

Dry Ampoule Containing 75 mg of Active Substance Per 10 ml

Composition

| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

Example 2

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

Example 3

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example 4

Tablet Containing 350 mg of Active Substance

Preparation:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example 5

Capsules Containing 50 mg of Active Substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing. This powder mixture is packed into size 3 hard gelatin capsules in a capsule filling machine.

Example 6

Capsules Containing 350 mg of Active Substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing. This powder mixture is packed into size 0 hard gelatin capsules in a capsule filling machine.

Example 7

Suppositories Containing 100 mg of Active Substance

Composition:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

The invention claimed is:

1. A pharmaceutical composition comprising a compound having the following structure 1.a

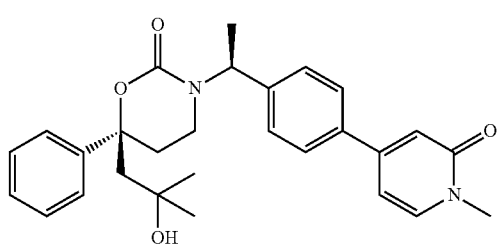

and/or a compound having the following structure

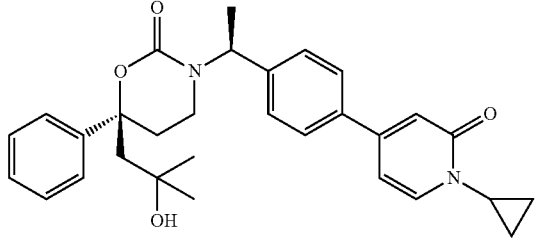

1.b or a pharmaceutically acceptable salt thereof in combination with at least one second therapeutic agent 2 which is suitable in the treatment of one or more conditions selected from type 1 diabetes mellitus, type 2 diabetes mellitus, impaired glucose tolerance (IGT), impaired fasting blood glucose (IFG), atherosclerose, glaucoma and hyperglycemia; wherein the at least one second therapeutic agent (2) is selected from the group consisting of:

2.a) biguanides, 2.b) sulfonylureas, 2.c) meglitinides, 2.d) thiazolidindiones, 2.e) alpha-glucosidase inhibitors, 2.f) insulins and insulin analogues, 2.g) dipeptidyl peptidase IV inhibitors (DPP IV inhibitors)

2.h) SGLT 2 inhibitors, 2.i) PPAR gamma/alpha modulators, 2.j) glucose-dependent insulinotropic polypeptide agonists, 2.k) beta-3 agonists, 2.l) GLP1 and GLP1 analogues, 2.m) PPAR gamma modulators, 2.n) HMG-CoA reductase inhibitors, and 2.o) PPAR delta modulators.

2. The pharmaceutical composition according to claim 1 characterized in that the at least one second therapeutic agent 2 is selected from the groups consisting of 2.a), 2.g) and 2.h).

3. A pharmaceutical composition comprising a compound having the following structure

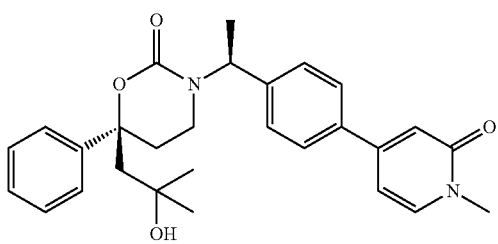

1.a and/or a compound having the following structure

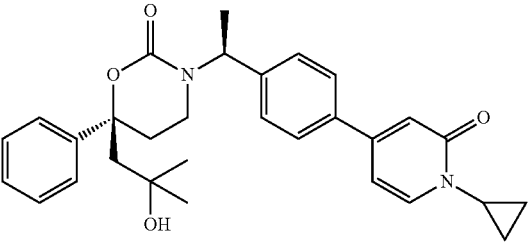

1.b or a pharmaceutically acceptable salt thereof in combination with at least one second therapeutic agent 2 which is suitable in the treatment of one or more conditions selected from type 1 diabetes mellitus, type 2 diabetes mellitus, impaired glucose tolerance (IGT), impaired fasting blood glucose (IFG), atherosclerose, glaucoma and hyperglycemia; characterized in that the at least one second therapeutic agent 2 is selected from the group consisting of metformin (2.a1), phenformin (2.a2), buformin (2.a3), chlorpropamide (2.b1), acetohexamide (2.b2), tolazamide (2.b3), glibenclamide (2.b4), tolbutamide (2.b5), glimepiride (2.b6), glipizide (2.b7), gliquidone (2.b8), glibornurid (2.b9), glyburide (2.b10), gliclazide (2.b11), nateglinide (2.c1), repaglinide (2.c2), mitiglinide (2.c3), pioglitazone (2.d1), rosiglitazone (2.d2), troglitazone (2.d3), ciglitazone (2.d4), miglitol (2.e1), acarbose (2.e2), voglibose (2.e3), insulin lispro (Humalog®) (2.f1), insulin aspartat (Novorapid®) (2.f2), insulin glulisine (Apidra®) (2.f3), regular insulin (2.f4), intermediate acting insulins like NPH-insulins and long acting insulins like lente (2.f5) and ultralente insulin (2.f6), insulin glargine (Lantus®) (2.f7), insulin detemir (Levemir®) (2.f8), denagliptin (2.g1), carmegliptin (2.g2), melogliptin (2.g3) sitagliptin (2.g4), vildagliptin (2.g5), saxagliptin (2.g6), linagliptin (2.g7), dutogliptin (2.g8), gemigliptin (2.g9), alogliptin (2.g10), 6-(4-ethylbenzyl)-4-(β-D-glucopyranos-1-yl)-2-methoxy-benzonitrile (2.h1), 2-(4-ethylbenzyl)-4-(β-D-glucopyranos-1-yl)-5-methoxy-benzonitrile (2.h2), 1-cyano-2-(4-ethylbenzyl)-4-(β-D-glucopyranos-1-yl)-5-methyl-benzene (2.h3), 2-(4-ethylbenzyl)-4-(β-D-glucopyranos-1-yl)-5-hydroxy-benzonitrile (2.h4), 2-(4-ethyl-benzyl)-4-(β-D-glucopyranos-1-yl)-benzonitrile (2.h5), 2-(4-cyclopropyl-benzyl)-4-(β-D-glucopyranos-1-yl)-benzonitrile (2.h6), 1-chloro-4-(β-D-glucopyranos-1-yl)-2-(4-ethynyl-benzyl)-benzene (2.h7), 1-chloro-4-(β-D-glucopyranos-1-yl)-2-[4-((R)-tetrahydrofuran-3-yloxy)-benzyl]-benzene (2.h8), 1-chloro-4-(β-D-glucopyranos-1-yl)-2-[4-((S)-tetrahydrofuran-3-yloxy)-benzyl]-benzene (2.h9), 1-methyl-2-[4-((R)-tetrahydrofuran-3-yloxy)-benzyl]-4-(β-D-glucopyranos-1-yl)-benzene (2.h10), 1-methyl-2-[4-((S)-tetrahydrofuran-3-yloxy)-benzyl]-4-(β-D-glucopyranos-1-yl)-benzene (2.h11), dapagliflozin (2.h12), atigliflozin (2.h13), remogliflozin (2.h14), sergliflozin (2.h15), canagliflozin (2.h16), tesaglitazar (2.i1), muraglitazar (2.i2), KRP297 (2.i3), pramlintide (2.j1), amlyin (2.j2), ritobegron (2.k1), YM 178 (2.k2), solabegron (2.k3), talibegronb (2.k4), N-5984 (2.k5), GRC-1087 (2.k6), rafabegron (2.k7), FMP825 (2.k8), exenatide (2.l1), liraglutide (2.l2), taspoglutide (2.l3), metaglidasen, (2.m1) simvastatin (2.n1), lovastatin (2.n2), provastatin (2.n3), GW 501516 (2.o1), GW 0742 (2.o2), L165041 (2.o3), LY 465608 (2.o4), and L-796449 (2.o5).

4. The pharmaceutical composition according to claim 3 characterized in that the at least one second therapeutic agent 2 is (2.a1), (2.d1), (2.g7) and (2.h9).

5. The pharmaceutical composition according to claim 3 characterized in that the composition is suitable for combined or simultaneous or sequential use of 1.a and/or 1.b and the at least one second therapeutic agent 2.

6. The pharmaceutical composition according to claim 3 characterized in that 1.a and/or 1.b and the at least one second therapeutic agent 2 are present in a single dosage form.

7. The pharmaceutical composition according to claim 1 characterized in that 1.a and/or 1.b and the at least one second therapeutic agent 2 are present each in a separate dosage form.

8. A method of using a compound having the following structure:

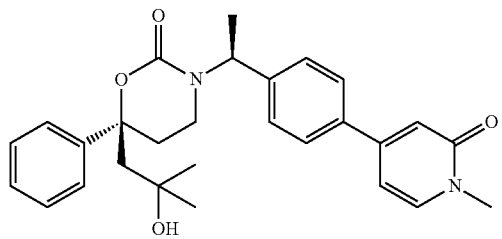

1.a and/or a compound having the following structure

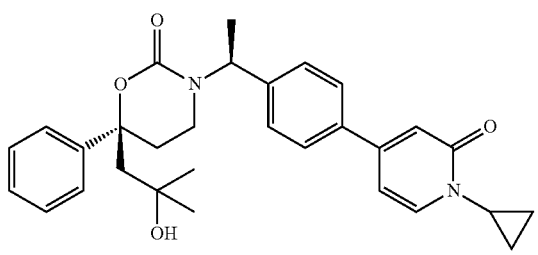

1.b or a pharmaceutically acceptable salt thereof, for
slowing the progression of, delaying or treating a metabolic disorder selected from the group consisting of type 1 diabetes mellitus, type 2 diabetes mellitus, impaired glucose tolerance, impaired fasting blood glucose, hyperglycemia, postprandial hyperglycemia, overweight, obesity and metabolic syndrome, or
improving glycemic control and/or for reducing of fasting plasma glucose, of postprandial plasma glucose and/or of glycosylated hemoglobin HbA1c, or
slowing, delaying or reversing progression from impaired glucose tolerance, impaired fasting blood glucose, insulin resistance and/or from metabolic syndrome to type 2 diabetes mellitus, or
slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease, or
reducing the weight or facilitating a reduction of the weight, or
slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion, or
slowing, delaying or treating diseases or conditions attributed to an abnormal accumulation of liver fat, or
maintaining and/or improving the insulin sensitivity and/or for treating hyperinsulinemia and/or insulin resistance, or
slowing progression of delaying or treating athersclerosis and complications of atherosclerosis, or
slowing progression of delaying or treating glaucoma and complications of glaucoma, or
slowing progression of delaying or treating dyslipidemia/hyperlipidemia and complications of dyslipidemia/hyperlipidemia;
improving glycemic control in patients with type 2 diabetes as an adjunct to diet and exercise, or
improving glycemic control in patients with type 2 diabetes
in a patient in need thereof characterized in that 1.a and/or 1.b is administered in combination or alternation with at least one second therapeutic agent with at least one second therapeutic agent 2 which is suitable in the treatment of one or more conditions selected from type 1 diabetes mellitus, type 2 diabetes mellitus, impaired glucose tolerance (IGT), impaired fasting blood glucose (IFG), atherosclerose, glaucoma and hyperglycemia.

9. A second therapeutic agent 2 according to claim 1, or a pharmaceutically acceptable salt thereof, for
slowing the progression of, delaying or treating a metabolic disorder selected from the group consisting of type 1 diabetes mellitus, type 2 diabetes mellitus, impaired glucose tolerance, impaired fasting blood glucose, hyperglycemia, postprandial hyperglycemia, overweight, obesity and metabolic syndrome, or
improving glycemic control and/or for reducing of fasting plasma glucose, of postprandial plasma glucose and/or of glycosylated hemoglobin HbA1c, or
slowing, delaying or reversing progression from impaired glucose tolerance, impaired fasting blood glucose, insulin resistance and/or from metabolic syndrome to type 2 diabetes mellitus, or
slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease, or
reducing the weight or facilitating a reduction of the weight, or
slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion, or
slowing, delaying or treating diseases or conditions attributed to an abnormal accumulation of liver fat, or
maintaining and/or improving the insulin sensitivity and/or for treating hyperinsulinemia and/or insulin resistance, or
slowing progression of delaying or treating athersclerosis and complications of atherosclerosis, or
slowing progression of delaying or treating glaucoma and complications of glaucoma, or slowing progression of delaying or treating dyslipidemia/
hyperlipidemia and complications of dyslipidemia/hy-
perlipidemia;
improving glycemic control in patients with type 2 diabe-
tes as an adjunct to diet and exercise, or
improving glycemic control in patients with type 2 diabe-
tes
in a patient in need thereof characterized in that second
therapeutic agent 2 is administered in combination or
alternation with 1.a and/or 1.b or a pharmaceutically
acceptable salt thereof.

10. A method of using a compound having the following structure:

1.a

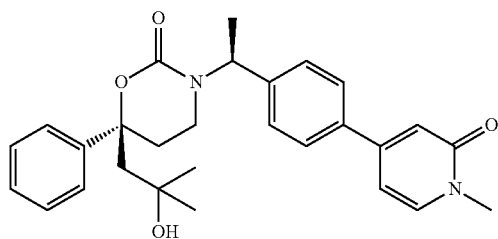

and/or a compound having the following structure 1.b

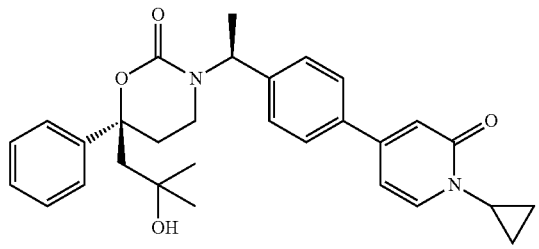

or a pharmaceutically acceptable salt thereof, for
slowing progression of delaying or treating athersclerosis
and complications of atherosclerosis, or
slowing progression of delaying or treating athersclerosis
and complications of glaucoma,
slowing progression of delaying or treating dyslipidemia/
hyperlipidemia and complications of dyslipidemia/hy-
perlipidemia;
improving glycemic control in patients with type 2 diabe-
tes as an adjunct to diet and exercise, or
improving glycemic control in patients with type 2 diabe-
tes
in a patient in need thereof.

11. A method of using the pharmaceutical composition according to claim 1 for
slowing the progression of, delaying or treating a meta-
bolic disorder selected from the group consisting of type
1 diabetes mellitus, type 2 diabetes mellitus, impaired
glucose tolerance, impaired fasting blood glucose,
hyperglycemia, postprandial hyperglycemia, over-
weight, obesity and metabolic syndrome; or
improving glycemic control and/or for reducing of fasting
plasma glucose, of postprandial plasma glucose and/or
of glycosylated hemoglobin HbA1c; or
slowing, delaying or reversing progression from impaired
glucose tolerance, insulin resistance and/or from meta-
bolic syndrome to type 2 diabetes mellitus; or
slowing the progression of, delaying or treating of a con-
dition or disorder selected from the group consisting of
complications of diabetes mellitus such as cataracts and
micro- and macrovascular diseases, such as nephropa-
thy, retinopathy, neuropathy, tissue ischaemia, arterio-
sclerosis, myocardial infarction, stroke and peripheral
arterial occlusive disease; or
reducing the weight or facilitating a reduction of the
weight; or
slowing, delaying or treating the degeneration of pancre-
atic beta cells and/or the decline of the functionality of
pancreatic beta cells and/or for improving and/or restor-
ing the functionality of pancreatic beta cells and/or
restoring the functionality of pancreatic insulin secre-
tion; or
slowing, delaying or treating diseases or conditions attrib-
uted to an abnormal accumulation of liver fat; or
maintaining and/or improving the insulin sensitivity and/or
for treating hyperinsulinemia and/or insulin resistance;
or
slowing progression of delaying or treating athersclerosis
and complications of atherosclerosis, or
slowing progression of delaying or treating athersclerosis
and complications of glaucoma, or
slowing progression of delaying or treating dyslipidemia/
hyperlipidemia and complications of dyslipidemia/hy-
perlipidemia;
improving glycemic control in patients with type 2 diabe-
tes as an adjunct to diet and exercise, or
improving glycemic control in patients with type 2 diabe-
tes in a patient in need thereof.

12. The method according to claim 8 wherein, the patient is an individual diagnosed of one or more of the conditions selected from the group consisting of overweight, obesity, visceral obesity and abdominal obesity.

13. The method according to claim 8, wherein the patient is an individual who shows one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in par-
ticular equal to or greater than 8.0%.

14. The method according to claim 8, wherein the patient is an individual wherein one, two, three or more of the following conditions are present:
(a) obesity, visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL,
(f) LDL-cholesterol blood levels ≥130 mg/dL.

15. The method according to claim 8, wherein the patient is an individual for whom monotherapy with metformin is con-traindicated and/or who has an intolerance against metformin at therapeutic doses.

16. The method according to claim 8, wherein the patient is an individual with insufficient glycemic control despite treat-ment with one or more antidiabetic drugs selected from the groups 2a) to 2n)

2.a) biguanides,
2.b) sulfonylureas,
2.c) meglitinides,
2.d) thiazolidindiones,
2.e) alpha-glucosidase inhibitors,
2.f) insulins and insulin analogues,
2.g) dipeptidyl peptidase IV inhibitors (DPP IV inhibitors)
2.h) SGLT 2 inhibitors,
2.i) PPAR gamma/alpha modulators,
2.j) glucose-dependent insulinotropic polypeptide agonists,
2.k) beta-3 agonists,
2.l) GLP1 and GLP1 analogues,
2.m) PPAR gamma modulators, and
2.n) HMG-CoA reductase inhibitors.

17. The method according to claim 8, wherein the at least one second therapeutic agent 2 is selected from (2.a1), (2.d1), (2.g7) and (2.h9).

\* \* \* \* \*